US 7,799,780 B2

(12) United States Patent
Herold et al.

(10) Patent No.: US 7,799,780 B2
(45) Date of Patent: Sep. 21, 2010

(54) CONDENSED IMIDAZOLE DERIVATIVES AS ALDOSTERONE SYNTHASE INHIBITORS

(75) Inventors: Peter Herold, Allschwil (CH); Robert Mah, Allschwil (CH); Vincenzo Tschinke, Allschwil (CH); Aleksandar Stojanovic, Allschwil (CH); Christiane Marti, Allschwil (CH); Stefan Stutz, Allschwil (CH); Bibia Bennacer, Allschwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/223,789

(22) PCT Filed: Apr. 12, 2007

(86) PCT No.: PCT/EP2007/053583

§ 371 (c)(1),
(2), (4) Date: Aug. 8, 2008

(87) PCT Pub. No.: WO2007/116097

PCT Pub. Date: Oct. 18, 2007

(65) Prior Publication Data

US 2009/0012068 A1    Jan. 8, 2009

(30) Foreign Application Priority Data

Apr. 12, 2006  (CH) ..................................... 617/06

(51) Int. Cl.
*C07D 498/04*   (2006.01)
*A61K 31/5365*  (2006.01)

(52) U.S. Cl. .................... 514/230.5; 544/105

(58) Field of Classification Search ............... 544/105; 514/230.5
See application file for complete search history.

(56) References Cited

U.S. PATENT DOCUMENTS 4,369,309 A    1/1983   Eto et al.
4,450,109 A    5/1984   Eto et al.

FOREIGN PATENT DOCUMENTS

| JP | 63145286 A * | 6/1988 |
| WO | WO 9700257 A1 * | 1/1997 |
| WO | 2005/118557 | 12/2005 |
| WO | 2005/118581 | 12/2005 |

OTHER PUBLICATIONS

International Search Report issued Jul. 9, 2007 in the International (PCT) Application PCT/EP2007/053583 of which the present application is the U.S. National Stage.
PCT Written Opinion in the International (PCT) Application PCT/EP2007/053583 of which the present application is the U.S. National Stage, Aug. 8, 2008.
Database WPI, Derwent Publications Ltd., AN 1988-209105, XP002439664 & JP 63 145286 A, Jun. 17, 1988.

* cited by examiner

*Primary Examiner*—Kahsay T Habte
(74) *Attorney, Agent, or Firm*—Wenderoth, Lind & Ponack, L.L.P.

(57) ABSTRACT

The application relates to novel heterocyclic compounds of the general formula (I) and salts, preferably pharmaceutically acceptable salts, thereof, in which R, $R^1$, $R^2$, $R^3$, Q, m and n have the meanings explained in detail in the description, a process for their preparation and the use of these compounds as medicaments, in particular as aldosterone synthase inhibitors.

18 Claims, No Drawings

CONDENSED IMIDAZOLE DERIVATIVES AS ALDOSTERONE SYNTHASE INHIBITORS

FIELD OF THE INVENTION

The invention relates to novel heterocyclic compounds, processes for preparing the compounds, pharmaceutical products containing them, and their use as active pharmaceutical ingredients, especially as aldosterone synthase inhibitors.

DETAILED DESCRIPTION OF THE INVENTION

The present invention relates firstly to compounds of the general formula

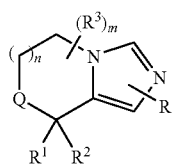

in which

R is deuterium, halogen, or hydrogen;

$R^1$ is aryl-$C_0$-$C_4$-alkyl or heterocyclyl-$C_0$-$C_4$-alkyl, which radicals may be substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl;

$R^2$ is a) deuterium, halogen, hydroxy, cyano or hydrogen; or
b) $C_2$-$C_8$ alkenyl, $C_2$-$C_8$ alkynyl, $C_1$-$C_8$ alkoxy, $C_1$-$C_4$ alkoxycarbonyl-$C_1$-$C_4$ alkyl, $C_1$-$C_8$ alkyl, $C_0$-$C_4$ alkylcarbonyl, aryl-$C_0$-$C_4$ alkyl, carboxy-$C_1$-$C_4$ alkyl, $C_3$-$C_8$ cycloalkyl or heterocyclyl-$C_0$-$C_4$ alkyl, which radicals may be substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl;

$R^3$ is $C_1$-$C_8$ alkyl;

Q is oxygen or sulphur;

m is a number 0, 1 or 2;

n is a number 0, 1 or 2;

and salts, preferably pharmaceutically acceptable salts, thereof where $R^1$ is not $C_1$-$C_8$ alkyl-substituted aryl if $R^2$ is hydrogen.

The term aryl stands for a mono-, bi- or tricyclic aromatic hydrocarbon complying with the Hückel rule which generally comprises 6-14, preferably 6-10, carbon atoms and is for example phenyl, naphthyl, e.g. 1- or 2-naphthyl or anthracenyl. Aryl having 6-10 carbon atoms, in particular phenyl or 1- or 2-naphthyl, is preferred. The stated radicals may be unsubstituted or substituted one or more times, e.g. once or twice, in which case the substituent may be in any position, e.g. in the o, m or p position of the phenyl radical or in the 3 or 4 position of the 1- or 2-naphthyl radical, and there may also be a plurality of identical or different substituents present. Examples of substituents on aryl radicals or the preferred phenyl or naphthyl radicals are: $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, tri-$C_1$-$C_4$ alkylsilyl, trifluoromethoxy or trifluoromethyl.

Aryl-$C_0$-$C_4$ alkyl is for example phenyl, naphthyl or benzyl.

The term heterocyclyl stands for a saturated, partially saturated or unsaturated, 4-8-membered, particularly preferably 5-membered, monocyclic ring system, for a saturated, partially saturated or unsaturated, 7-12-membered, particularly preferably 9-10-membered, bicyclic ring system and also for a partially saturated or unsaturated, 9-12-membered tricyclic ring system which comprises an N, O or S atom in at least one of the rings, it being possible for an additional N, O or S atom to be present in one ring. Said radicals may be unsubstituted or substituted one or more times, e.g. once or twice, and there may also be a plurality of identical or different substituents present. Examples of substituents on heterocyclyl radicals are: $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl.

Saturated heterocyclyl-$C_0$-$C_4$ alkyl is for example azepanyl, azetidinyl, aziridinyl, 3,4-dihydroxy-pyrrolidinyl, 2,6-dimethylmorpholinyl, 3,5-dimethylmorpholinyl, dioxanyl, [1,4]dioxepanyl, dioxolanyl, 4,4-dioxothiomorpholinyl, dithianyl, dithiolanyl, 2-hydroxymethylpyrrolidinyl, 4-hydroxypiperidinyl, 3-hydroxypyrrolidinyl, 4-methylpiperazinyl, 1-methylpiperidinyl, 1-methyl-pyrrolidinyl, morpholinyl, oxathianyl, oxepanyl, 2-oxo-azepanyl, 2-oxo-imidazolidinyl, 2-oxo-oxazolidinyl, 2-oxo-piperidinyl, 4-oxo-piperidinyl, 2-oxo-pyrrolidinyl, 2-oxo-tetrahydro-pyrimidinyl, 4-oxo-thiomorpholinyl, piperazinyl, piperidinyl, pyrrolidinyl, tetrahydrofuranyl, tetrahydropyranyl, tetrahydrothiophenyl, tetrahydrothiopyranyl, thiepanyl or thiomorpholinyl.

Partially saturated bicyclic heterocyclyl-$C_0$-$C_4$ alkyl is for example 3,4-dihydro-2H-benzo[1,4]oxazinyl, 4,5,6,7-tetrahydrobenzofuranyl or 4,5,6,7-tetrahydrobenzothiazolyl.

Unsaturated bicyclic heterocyclyl-$C_0$-$C_4$ alkyl is for example benzofuranyl, benzoimidazolyl, benzo[d]isothiazolyl, benzo[d]isoxazolyl, benzo[b]thiophen-yl, quinolinyl, imidazo[1,5-a]pyridinyl, indazolyl, indolyl or isoquinolinyl.

Unsaturated monocyclic heterocyclyl-$C_0$-$C_4$ alkyl is for example imidazolyl, oxazolyl, pyridyl, pyrrolyl, tetrazolyl, thiazolyl or thiophenyl.

$C_2$-$C_8$ alkenyl is for example ethenyl, propenyl, isopropenyl, butenyl, isobutenyl, secondary butenyl, tertiary butenyl, or a pentenyl, hexenyl or heptenyl group.

$C_2$-$C_8$ alkynyl is for example ethynyl, propynyl, butynyl, or a pentynyl, hexynyl or heptynyl group.

$C_1$-$C_8$ alkoxy is for example $C_1$-$C_5$ alkoxy such as methoxy, ethoxy, propoxy, isopropoxy, butoxy, isobutoxy, secondary butoxy, tertiary butoxy or pentoxy, but may also be a hexoxy or heptoxy group.

$C_1$-$C_8$ alkoxycarbonyl is preferably $C_1$-$C_4$ alkoxycarbonyl such as methoxycarbonyl, ethoxy-carbonyl, propoxycarbonyl, isopropoxycarbonyl, butoxycarbonyl, isobutoxycarbonyl, secondary butoxycarbonyl or tertiary butoxycarbonyl.

$C_1$-$C_4$ alkoxycarbonyl-$C_1$-$C_4$ alkyl is for example methoxycarbonylmethyl or ethoxycarbonyl-methyl, 2-methoxycarbonylethyl or 2-ethoxycarbonylethyl, 3-methoxycarbonylpropyl or 3-ethoxycarbonylpropyl or 4-ethoxycarbonylbutyl.

$C_1$-$C_8$ alkyl may be straight-chain or branched and/or bridged and is for example methyl, ethyl, propyl, isopropyl, butyl, isobutyl, secondary butyl, tertiary butyl, or a pentyl, hexyl or heptyl group.

$C_0$-$C_8$ alkylcarbonyl or preferably $C_0$-$C_4$ alkylcarbonyl is for example formyl, acetyl, propionyl, propylcarbonyl, isopropylcarbonyl, butylcarbonyl, isobutylcarbonyl, secondary butylcarbonyl or tertiary butylcarbonyl.

Carboxy-$C_1$-$C_4$ alkyl is for example carboxymethyl, 2-carboxyethyl, 2- or 3-carboxypropyl, 2-carboxy-2-methylpropyl, 2-carboxy-2-ethylbutyl, or 4-carboxybutyl, in particular carboxy-methyl.

$C_3$-$C_8$ cycloalkyl is preferably 3-, 5- or 6-membered cycloalkyl, such as cyclopropyl, cyclo-pentyl, cyclohexyl.

Halogen is for example fluorine, chlorine, bromine or iodine.

The compound groups mentioned below are not to be regarded as closed; on the contrary, parts of these compound groups may be replaced by one another or by the definitions given above, or be omitted, in a meaningful way, e.g. to replace general by more specific definitions. The definitions mentioned apply within the scope of general chemical principles such as, for example, the usual valencies of atoms.

R is preferably deuterium or hydrogen.

$R^1$ is preferably aryl, very particularly preferably mono-, di- or tri-substituted phenyl or mono-, di- or tri-substituted naphthyl, or heterocyclyl, very particularly preferably optionally mono-, di- or tri-substituted benzofuranyl, benzo[b]thiophenyl, benzoimidazolyl, benzo[d]isothiazolyl, benzo[d]isoxazolyl, benzo[b]thiophenyl, imidazolyl, indazolyl, indolyl, oxazolyl, pyridyl, pyrrolyl, thiazolyl or thiophenyl.

$R^2$ is preferably $C_1$-$C_8$ alkoxy, hydroxy, $C_1$-$C_8$ alkyl, optionally substituted aryl-$C_0$-$C_4$ alkyl, deuterium, halogen, cyano or hydrogen.

$R^3$ is preferably $C_1$-$C_4$ alkyl.

n is preferably a number 0 or 1. n is particularly preferably the number 1.

Preferred substituents for aryl or heterocyclyl are $C_1$-$C_8$ alkoxy, $C_1$-$C_8$ alkyl, $C_1$-$C_8$ alkyl-carbonyl, $C_1$-$C_8$ alkylsulphonyl, optionally substituted aryl, cyano, halogen, optionally substituted heterocyclyl, nitro, oxide, trifluoromethyl, trifluoromethoxy or trimethylsilanyl. Very particularly preferred substituents for aryl or heterocyclyl are acetyl, bromine, chlorine, cyano, fluorine, methanesulphonyl, methoxy, nitro, oxazolyl, oxide, optionally substituted phenyl, optionally substituted tetrazolyl, optionally substituted thiazolyl or optionally substituted thiophenyl.

It is likewise preferred for $R^1$ to be a mono-, di- or tri-substituted unsaturated heterocyclyl substituent, where the substituents are preferably selected from the group consisting of $C_1$-$C_8$ alkyl, $C_1$-$C_8$ alkoxy, $C_1$-$C_8$ alkoxycarbonyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy and trifluoro-methyl.

Particularly preferred compounds of the formula (I) are those of the general formula (Ia) and salts, preferably pharmaceutically acceptable salts, thereof,

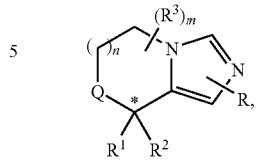

in which R, $R^1$, $R^2$, $R^3$, Q, m and n have the meanings indicated above for compounds of the formula (I), and where the above preferences apply analogously.

* designates an asymmetric carbon atom.

The compounds of the formula (I) or (Ia) which possess at least one asymmetric carbon atom can exist in the form of optically pure enantiomers, mixtures of enantiomers, or racemates. Compounds having a second asymmetric carbon atom can exist in the form of optically pure diastereomers, mixtures of diastereomers, diastereomeric racemates, mixtures of diastereomeric racemates, or meso compounds. The invention embraces all of these forms. Mixtures of enantiomers, racemates, mixtures of diastereomers, diastereomeric racemates, or mixtures of diastereomeric racemates can be fractionated by conventional methods, such as by racemate resolution, column chromatography, thin-layer chromatography, HPLC and the like.

The compounds of the formula (Ia) have at least one asymmetric carbon atom, which is labelled "*". A compound of the formula (Ia) is to be understood as a compound having a specific configuration around the designated asymmetric carbon atom. If a synthesis method is used which leads to racemic compounds, the racemate resolution is carried out in accordance with conventional methods, such as via a chiral HPLC column. Compounds of the formula (Ia) as described in the present invention exhibit a pronounced aldosterone synthase and/or 11-β-hydroxylase inhibitory activity and a low aromatase inhibitory activity. The aforementioned aromatase inhibitory activity can, as the skilled worker is well aware and as described below, be comfortably determined using the commercial Cyp19 enzyme inhibition kit, preferably the Cyp19/methoxy-4-trifluoromethyl-coumarin (MFC) high throughput inhibition kit (Becton Dickinson Biosciences, San Jose, Calif., USA) as described hereafter. In the abovementioned inhibition kit, compounds of the formula (Ia) have an activity which is at least 10 times lower preferably 20 times lower, but more preferably 40 times lower than the compounds of the formula (Ia) with the opposite configuration around the asymmetric carbon atom labelled "*". A lower inhibiting activity corresponds to a higher $IC_{50}$ value.

CYP19 inhibition:

| Example number | $IC_{50}$ value [nM] |
| --- | --- |
| 24 | 2769.0 |
| antipode of 24 | 7.1 |

The expression "pharmaceutically acceptable salts" embraces salts with organic or inorganic acids, such as hydrochloric acid, hydrobromic acid, nitric acid, sulphuric acid, phosphoric acid, citric acid, formic acid, maleic acid, acetic acid, succinic acid, tartaric acid, methane-sulphonic acid, p-toluenesulphonic acid and the like. Salts of compounds containing salt-forming groups are, in particular, acid addition salts, salts with bases or else, if appropriate, if two or more salt-forming groups are present, are mixed salts or inner salts.

The compounds of the formula (I) or (Ia) can be prepared in an analogous manner to the preparation processes disclosed per se in the literature by JP63145286 (Scheme).

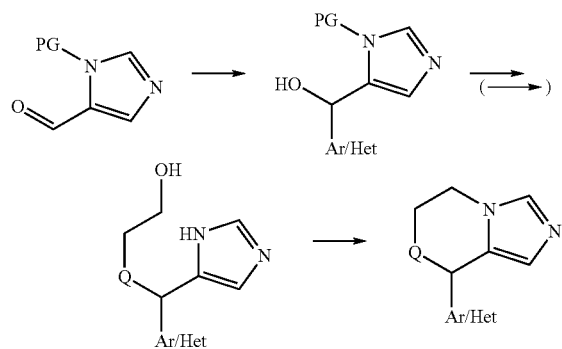

Details of the specific preparation variants can be found in the examples.

The compounds of the formula (I) or (Ia) can also be prepared in optically pure form. Separation into antipodes is possible by methods known per se, either, preferably, at an early stage in synthesis, by salt formation with an optically active acid such as, for example, (+)- or (−)-mandelic acid and separation of the diastereomeric salts by fractional crystallization, or, preferably, at a fairly late stage, by derivatization with a chiral auxiliary component, such as, for example, (+)- or (−)-camphanyl chloride and separation of the diastereomeric products by chromatography and/or crystallization and subsequent cleavage of the bond to the chiral auxiliary. The pure diastereomeric salts and derivatives can be analysed to determine the absolute configuration of the compound present, using customary spectroscopic methods, with single-crystal X-ray spectroscopy representing one particularly appropriate method.

Salts are primarily the pharmaceutically acceptable or non-toxic salts of compounds of the formula (I) or (Ia). Such salts are formed for example by compounds of the formula (I) or (Ia) containing an acidic group, such as a carboxyl or sulpho group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxyl-lower alkyl)amines, such as ethanolamine, diethanolamine or triethanolamine, tris(hydroxylmethyl)methylamine or 2-hydroxyl-tertiary-butylamine, N,N-di-lower alkyl-N-(hydroxyl-lower alkyl)amine, such as N,N-di-N-dimethyl-N-(2-hydroxyl-ethyl)amine, or N-methyl-D-glucamine, or quaternary ammonium hydroxides, such as tetrabutylammonium hydroxide. The compounds of the formula (I) or (Ia) containing a basic group, such as an amino group, can form acid addition salts, with suitable inorganic acids for example, such as hydrohalic acid, such as hydrochloric acid, hydrobromic acid, or sulphuric acid with replacement of one or both protons, phosphoric acid with replacement of one or more protons, orthophosphoric acid or metaphosphoric acid for example, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxylmaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, such as the α-amino acids specified earlier on, and also methanesulphonic acid, ethanesulphonic acid, 2-hydroxylethanesulphonic acid, ethane-1,2-disulphonic acid, benzene-sulphonic acid, 4-toluenesulphonic acid, naphthalene-2-sulphonic acid, 2- or 3-phosphoglycerate, glucose 6-phosphate, N-cyclohexylsulphamic acid (to form cyclamates), or with other acidic organic compounds, such as ascorbic acid. Compounds of the formula (I) or (Ia) containing acidic and basic groups can also form inner salts.

Isolation and purification can also be carried out using pharmaceutically unsuitable salts.

The compounds of the formula (I) or (Ia) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl)-alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the close relationship between a free compound, a prodrug derivative and a salt compound, a defined compound in this invention also includes its prodrug derivative and salt form, insofar as this is possible and appropriate.

Aldosterone is a steroidal hormone which is synthesized in the zona glomerulosa cells of the adrenal cortex by the enzyme aldosterone synthase (CYP11B2). Aldosterone production and secretion is regulated by the adrenocorticotropic hormone (ACTH), angiotensin II, potassium and sodium ions. The primary biological function of aldosterone is the regulation of the salt balance, with aldosterone controlling the reabsorption of sodium ions from the renal filtrate and the secretion of potassium ions into the renal filtrate. The state of excessive aldosterone secretion, also called hyperaldosteronism, can lead to high blood pressure, hypokalaemia, alkalosis, muscle weakness, polyuria, polydipsia, oedemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The compounds described can be employed for preventing, for delaying the progression of or treating states such as hypokalaemia, hypertension, congestive heart failure, acute and—in particular—chronic renal failure, cardiovascular restenosis, atherosclerosis, metabolic syndrome (syndrome X), adiposity (obesity), vasculitis, primary and secondary hyperaldosteronism, nephropathy, myocardial infarction, coronary heart disease, increased collagen formation, fibrosis, vascular and coronary tissue changes (remodelling) secondary to high blood pressure, endothelial dysfunction, and oedemas secondary to cirrhosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is regulated by ACTH. The primary biological function of cortisol is to regulate the production and the provision of carbohydrates for the brain and other metabolically active tissues. Increased cortisol production and secretion is a normal physiological response to stress and leads to the essential mobilization of fats, proteins and carbohydrates to cover increased physical energy demand. Chronically excessive cortisol release describes the condition of Cushing's syndrome. Cushing's syndrome may come about on the one hand as a result of cortisol hypersynthesis, which may be generated by an adrenocortical tumour, or on the other hand as the consequence of excessive stimulation of the adrenal cortex by ACTH. The first form is referred to as primary hypercortisolism, the second form as secondary hypercortisolism. An excessive and persistent cortisol secretion may also accompany a stress response, which can lead to depression and the suppression of the immune system.

The chemical compounds described in this invention inhibit the enzyme 11-β-hydroxylase (CYP11B1) and may therefore, owing to the inhibition of cortisol synthesis, be employed for preventing, for delaying the progression of or treating Cushing's syndrome and also the physical and mental consequences of excessive and persistent cortisol secretion in states of stress.

The inhibition of aldosterone synthase (CYP11B2), as well as 11-β-hydroxylase (Cyp11B1) and aromatase (Cyp19) by herein described compounds may be measured by the following in vitro assay.

The cell line NCI-H295R was originally derived from an adrenal carcinoma and was subsequently characterized in the literature for the inducible secretion of steroidal hormones and the presence of the key enzymes necessary for steroidogenesis. These include Cyp11A (cholesterol side-chain cleavage), Cyp11B1 (steroid 11β-hydroxylase), Cyp11B2 (aldosterone synthase), Cyp17 (steroid 17α-hydroxylase and 17,20 lyase), Cyp19 (aromatase), Cyp21B2 (steroid 21-hydroxylase) and 3β-HSD (hydroxysteroid dehydrogenase). The cells have the physiological characteristics of zonally undifferentiated human fetal adrenal cells, with the ability to produce the steroid hormones of each of the three phenotypically distinct zones found in the adult adrenal cortex.

The NCI-H295R cells (American Type Culture Collection, ATCC, Rockville, Md., USA) are cultured in Dulbecco's Modified Eagle'Ham F-12 medium (DME/F12) that is supplemented with Ultroser SF serum (Soprachem, Cergy-Saint-Christophe, France) as well as insulin, transferrin, selenite (I-T-S, Becton Dickinson Biosiences, Franklin Lakes, N.J., USA) and antibiotics in 75 cm² cell culture flasks at a temperature of 37° C. and a 95% air/5% $CO_2$ humidified atmosphere. The cells are subsequently transferred to a 24-well plate and seeded in the presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence of cell stimulatory agents. The test compound is added in a concentration range of 0.2 nanomolar to 20 micromolar. Angiotensin-II (e.g. at 10 or 100 nanomolar concentration), potassium ions (e.g. at 16 millimolar), forskolin (e.g. at 10 micromolar) or a combination of two agents may serve as cell-stimulatory agents. The cellular secretion of aldosterone, cortisol, corticosterone and estradiol/estrone into the cell culture medium can be quantitatively assessed with commercially available radioimmunoassays and specific anti-bodies (e.g. Diagnostics Products Corporation, Los Angeles, Calif., USA) according to the manufacturer's instructions.

The degree of secretion of a selective steroid is used as a measure of enzyme activity, respectively enzyme inhibition, in the presence or absence of a test compound. The dose-dependent enzyme inhibitory activity of a compound is reflected in an inhibition curve that is characterized by an $IC_{50}$ value. The $IC_{50}$ values for active test compounds are generated by simple linear regression analysis to establish inhibition curves without data weighting. The inhibition curve is generated by fitting a 4-parameter logistic function to the raw data of the samples using the least squares approach. The function is described as follows:

$$Y=(d-a)/((1+(x/c)^{-b})+a)$$

with:

a=minimum b=slope c=$IC_{50}$ d=maximum x=inhibitor concentrations

The compounds of the present invention show in the herein described in vitro test systems inhibitory activities with $IC_{50}$ values for aldosterone synthesis inhibition ranging from $10^{-4}$ to $10^{-10}$ mol/l, and $IC_{50}$ values for cortisol synthesis inhibition ranging from $10^{-4}$ to $10^{-10}$ mol/l.

Additionally, the in vitro inhibition of aromatase activity of the compounds of the present invention can be demonstrated by using a commercial Cyp19 enzyme inhibition kit. The Cyp19/methoxy-4-trifluoromethyl-coumarin (MFC) high throughput inhibition kit (Becton Dickinson Biosciences, San Jose, Calif., USA), for example, is designed to screen for potential inhibitors of Cyp19 catalytic activity in a 96-well format. The kit includes recombinant human Cyp19 enzyme in the form of supersomes, a fluorescent P450 substrate, an NADPH regenerating system, a reaction buffer and a stop reagent. MFC, the fluorogenic substrate is rapidly converted by Cyp19 supersomes to the highly fluorescent product 7-hydroxy-4-trifluoromethyl coumarin (7-HFC). The execution of the assay in the presence of various concentrations of inhibitor compounds ranging from 0.2 nanomolar to 20 millimolar occurs according to the manufacturer's instructions.

The inhibition curve is generated by fitting a 4-parameter logistic function to the raw data of the samples using the least squares approach. The function is described as follows:

$$Y=(d-a)/((1+(x/c)^{-b})+a)$$

with:

a=minimal data values b=slope c=IC$_{50}$ d=maximal data values x=inhibitor concentrations The aldosterone- and corticosterone-suppressing activity of herein described compounds may be assessed with the following in vivo protocol.

Adult male Wistar rats weighing between 250 and 350 grams are kept under the usual 12-hour light and 12-hour dark conditions at a temperature of 23° C.±2° C. On the first day of the experiment, the animals receive a subcutaneous injection of a depot ACTH product in a dose of 1.0 mg/kg weight (SYNACTHEN-Depot, Novartis, Basel, CH) 16 hours prior to the administration of a test compound. Pilot studies showed that this ACTH dose significantly increased plasma aldosterone and corticosterone levels by 5- to 20-fold over a period of at least 18 hours. An alternative method to stimulate aldosterone secretion consists in subjecting rats to a low salt diet for 48 hours and applying the diuretic furosemide at 10 mg/kg by subcutaneous or intraperitoneal administration 16 hours, respectively 2 hours prior to the start of the experiment. On the second day of the experiment, the animals are divided into test groups of 5 animals and subjected to a first bleed 1 hour prior to the administration of test compound. Subsequently, and 16 hours after the injection of the ACTH product, the animals receive either vehicle or test compound dissolved in vehicle in a variable dose range from 0.02 to 20 mg/kg by oral gavage. The animals are bled two more times from the vena subclavia under isoflurane anaesthesia 2 and 6 hours after dosing. The blood is collected in heparin-treated tubes. The plasma samples are obtained by centrifugation and stored at −20° C. An alternative method to bleed animals time-dependently consists in using animals that are chronically carotid catheterized which allows the periodical sampling of up to 0.2 ml of blood using an AccuSampler (DiLab Europe, Lund, Sweden). The blood sampling with the AccuSampler may occur 1 hour prior to the administration of a test compound and 2, 4, 6, 8, 12, 16 and 24 hours thereafter. The blood samples are anticoagulated with heparin and centrifuged. The aldosterone and corticosterone concentrations of the plasma samples can be determined with a radioimmunoassay as described above for the in vitro test systems.

The selective suppression of plasma steroid levels as for instance aldosterone in comparison to corticosterone may serve as a measure for in vivo bioavailability and pharmacodynamic enzyme inhibitory activity of the herein described compounds. The evaluation of the data may occur relative to the application of vehicle or quantitatively by determination of the area under the curve (AUC).

Examples of suppression of aldosterone and corticosterone levels:

| Compound of Example | Dose (mg/kg p.o.) | Aldosterone levels (% change[+] at 2h) | Corticosterone levels (% change[+] at 2h) |
| --- | --- | --- | --- |
| 2 | 4 | −56 | −22 |
| 4 | 4 | −19 | −10 |
| 18 | 4 | −33 | 4 |
| 19 | 4 | −65 | 1.7 |

[+]The resulting changes in plasma aldosterone, respectively corticosterone, levels upon oral administration of a test compound are expressed as percent (%) change that is defined by the ratio of the [(plasma steroid level 2 hours after compound administration) - (plasma steroid level 1 hour prior to compound administration)] divided by (plasma steroid level 1 hour prior to compound administration).

In order to achieve the desired effects in a patient to be treated, the compounds of the pre-sent invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatine capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatine, disintegrants such as potato starch or crosslinked polyvinylpyrrolidone (PVPP) and lubricants such as stearic acid or magnesium stearate.

Examples of excipients suitable for soft gelatine capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semi-liquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

as therapeutic combination in the form of a product or of a kit which is composed of individual components consisting of a compound described herein, in free form or as pharmaceutically acceptable salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.

as method for combined use, such as, for example, in simultaneous or sequential succession, of a therapeutically effective amount of a compound described herein, in free or in pharmaceutically acceptable salt form, and of a second active ingredient with blood pressure-lowering, inotropic, antidiabetic, obesity-reducing or lipid-lowering effect.

The compounds described herein and their pharmaceutically acceptable salts can be used in combination with (i) one or more blood pressure-lowering active ingredients, as such for example:
  renin inhibitors such as aliskiren;
  angiotensin II receptor blockers such as candesartan, irbesartan, olmesartan, losartan, valsartan, telmisartan etc.;
  ACE inhibitors such as quinapril, ramipril, trandolapril, lisinopril, captopril, enalapril etc.;
  calcium antagonists such as nifedipine, nicardipine, verapamil, isradipine, nimodipine, amlodipine, felodipine, nisoldipine, diltiazem, fendiline, flunarizine, perhexyline, gallopamil etc.;
  diuretics such as hydrochlorothiazide, chlorothiazide, acetazolamide, amiloride, bumetanide, benzthiazide, etacrynic acid, furosemide, indacrinone, metolazone, triamterene, chlorthalidone, etc.;
  aldosterone receptor blockers such as spironolactone, eplerenone;
  endothelin receptor blockers such as bosentan;
  phosphodiesterase inhibitors such as aminone, sildenafil;
  direct vasodilators such as dihydralazine, minoxidil, pinacidil, diazoxide, nitroprusside, flosequinan etc.;
  α- and β-receptor blockers such as phentolamine, phenoxybenzamine, prazosin, doxazosin, terazosin, carvedilol, atenolol, metoprolol, nadolol, propranolol, timolol, carteolol etc.;
  neutral endopeptidase (NEP) inhibitors;
  sympatholytics such as methyldopa, clonidine, guanabenz, reserpine (ii) one or more agents having inotropic activity, as such for example:
  cardiac glycosides such as digoxin;
  β-receptor stimulators such as dobutamine;
  thyroid hormone such as thyroxine (iii) one or more agents having antidiabetic activity, as such for example:
  insulins such as insulin aspart, insulin human, insulin lispro, insulin glargine and further fast-, medium- and long-acting insulin derivatives and combinations
  insulin sensitizers such as rosiglitazone, pioglitazone;
  sulphonylureas such as glimepiride, chlorpropamide, glipizide, glyburide etc.;
  biguanides such as metformin;
  glucosidase inhibitors such as acarbose, miglitol;
  meglitinides such as repaglinide, nateglinide;

(iv) one or more obesity-reducing ingredients, as such for example:
  lipase inhibitors such as orlistat;
  appetite suppressants such as sibutramine, phentermine;

(v) one or more lipid-lowering ingredients, such as, for example,
  HMG-CoA reductase inhibitors such as lovastatin, fluvastatin, pravastatin, atorvastatin, simvastatin, rosuvastatin etc.;
  fibrate derivatives such as fenofibrate, gemfibrozil etc.;
  bile acid-binding active ingredients such as colestipol, colestyramine, colesevelam;
  cholesterol absorption inhibitors such as ezetimibe;
  nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The compounds described herein and their pharmaceutically acceptable salts can additionally be used in combination with (i) a diagnostic test system which permits quantitative determination of the plasma aldosterone level (PAC, plasma aldosterone concentration)

(ii) a diagnostic test system which permits quantitative determination of the plasma renin level (PRC, plasma renin concentration)

(iii) a diagnostic test system which permits quantitative determination of the plasma renin activity (PRA, plasma renin activity)

(iv) a diagnostic test system which permits quantitative determination of the plasma aldosterone/renin level (ARC, aldosterone renin concentration)

(v) a diagnostic test system which permits quantitative determination of the plasma aldosterone/renin activity (ARR, aldosterone to renin activity ratio)

(vi) a diagnostic test system which permits quantitative determination of the plasma cortisol level (PCC, plasma cortisol concentration)

Such diagnosis-therapy combinations can be used separately or in products which comprise a plurality of components.

EXAMPLES

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program.

HPLC gradient on Hypersil BDS C-18 (5 μm); column: 4×125 mm:

90% water*/10% acetonitrile*to 0% water*/100% acetonitrile*in 5 minutes+2.5 minutes(1.5 ml/min)

The abbreviations used are as follows:

Rf ratio of distance traveled by a substance to distance of the eluent from the starting point in thin-layer chromatography Rt retention time of a substance in HPLC (in minutes)

m.p. melting point (temperature)

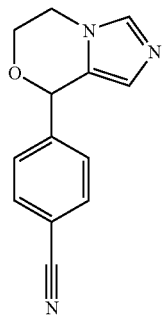
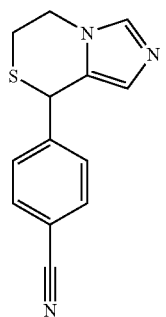
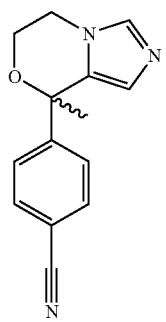
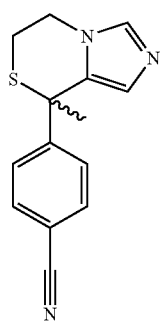
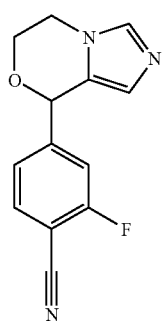
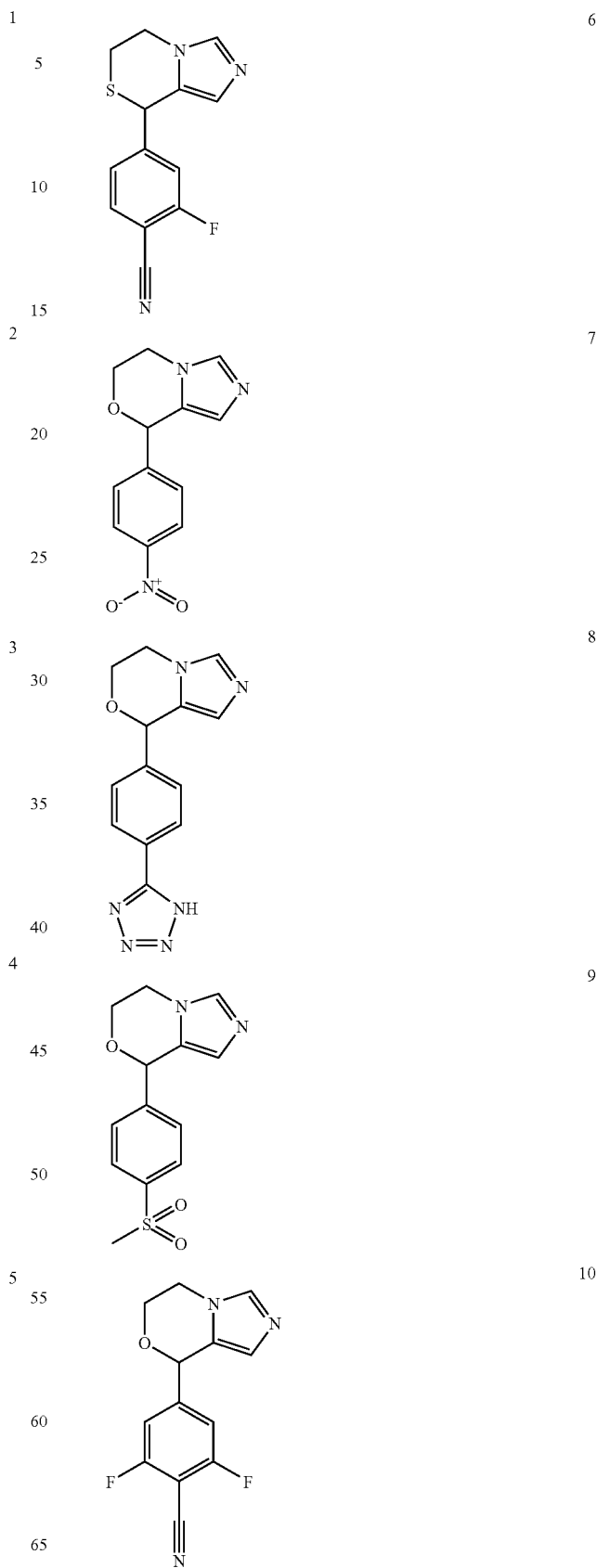

-continued
11 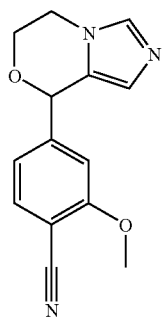
12 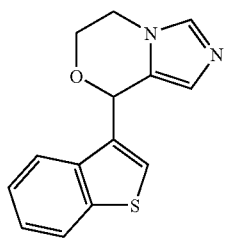
13 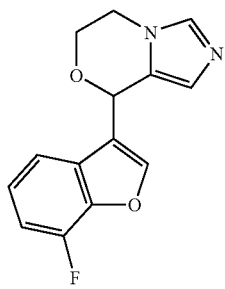
14 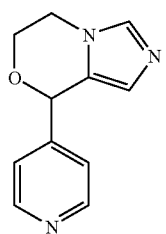
15 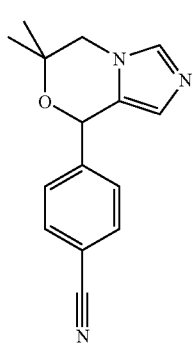
-continued
16 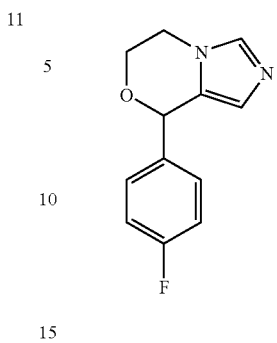
17 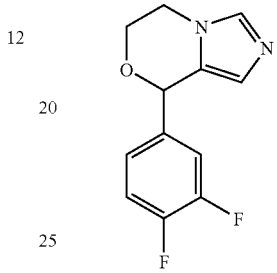
18 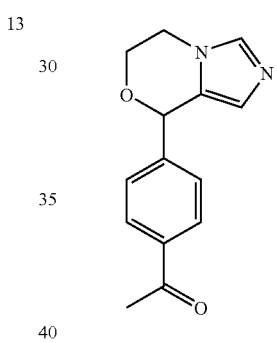
19 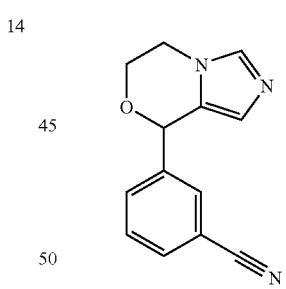
20 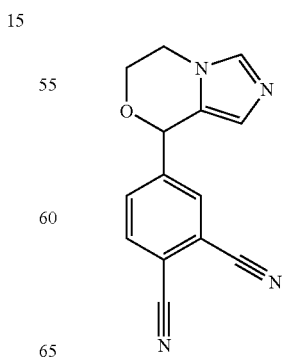

17

-continued

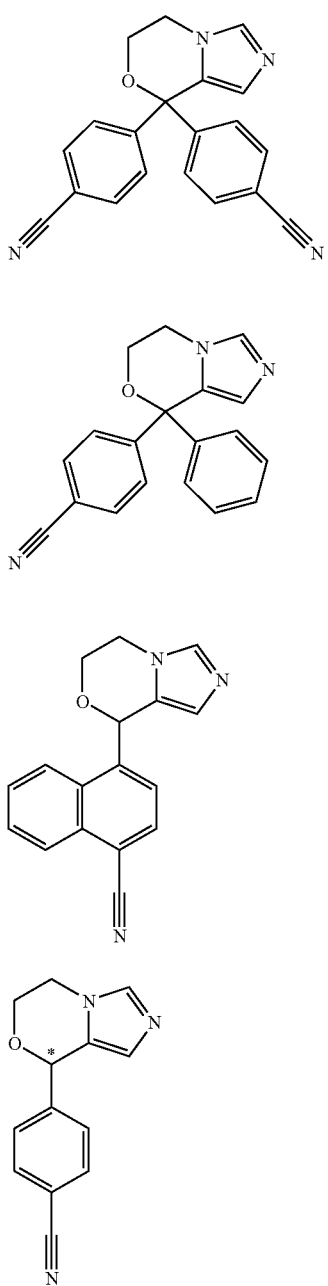

21

22

23

24

Example 1

4-(5,6-Dihydro-8H-imidazo[5,1-c][1,4]oxazin-8-yl)benzonitrile

A solution of 1.20 mmol of 2-[(4-cyanophenyl)-(3H-imidazol-4-yl)methoxy]ethyl methane-sulphonate in 10 ml of acetonitrile is heated to reflux for 24 hours. The reaction mixture is cooled to room temperature and evaporated. The title compound is obtained as a white solid from the residue by flash chromatography (SiO$_2$ 60F). Rf=0.14 (dichloromethane-2M ammonia in ethanol 95:5); Rt=4.29.

18

The starting materials are prepared as follows:

a) 2-[(4-Cyanophenyl)-(3H-imidazol-4-yl)methoxy]ethyl methanesulphonate 1.44 mmol of diisopropylethylamine and 1.20 mmol of methanesulphonyl chloride are added to a solution of 1.20 mmol of 4-[(2-hydroxyethoxy)-(3H-imidazol-4-yl)methyl]benzonitrile in 10 ml of dichloromethane at 0° C. The reaction mixture is stirred at 0° C. for 3 hours, tipped into water and extracted with dichloromethane. The combined organic phases are washed with brine, dried over sodium sulphate and evaporated. The crude title compound is used without further purification in the next stage.

b) 4-[(2-Hydroxyethoxy)-(3H-imidazol-4-yl)methyl]benzonitrile 2.45 mmol of sodium borohydride are added to a solution of 1.63 mmol of ethyl [(4-cyano-phenyl)-1-(trityl-1H-imidazol-4-yl)methoxy]acetate in 10 ml of ethanol at room temperature. The reaction mixture is stirred at room temperature for 16 hours and then evaporated. The residue is taken up in dichloromethane and saturated aqueous sodium bicarbonate solution, the phases are separated, and the aqueous phase is back-extracted with dichloromethane. The combined organic phases are dried with sodium sulphate and evaporated. The title compound is obtained as a white solid from the residue by flash chromatography (SiO$_2$ 60F). Rf=0.10 (ethyl acetate-heptane 1:2); Rt=7.39.

c) Ethyl [(4-cyanophenyl)-(1-trityl-1H-imidazol-4-yl)methoxy]acetate 5.00 mmol of 4-[hydroxy-(1-trityl-1H-imidazol-4-yl)methyl]benzonitrile are added to a mixture of 6.50 mmol of sodium hydride (60% dispersion in paraffin) in 20 ml of N,N-dimethyl-formamide at 0° C. The reaction mixture is stirred at 0° C. for 1 hour and then bromoacetic acid is added dropwise. The reaction mixture is stirred at room temperature for 16 hours, poured into water and extracted with tert-butyl methyl ether. The combined organic phases are washed with brine, dried with sodium sulphate and evaporated. The title compound is obtained as an amber-coloured oil from the residue by flash chromatography (SiO$_2$ 60F). Rf=0.42 (ethyl acetate-heptane 1:2); Rt=8.00.

d) 4-[Hydroxy-(1-trityl-1H-imidazol-4-yl)methyl]benzonitrile

A solution of 14.80 mmol of 4-iodobenzonitrile [3058-39-7] in 20 ml of tetrahydrofuran is cooled to −30° C., and 14.80 mmol of i-propylmagnesium chloride (2M in tetrahydrofuran) are added. The mixture is stirred at −30° C. for 60 minutes and a solution, precooled to −30° C., of 11.84 mmol of 1-trityl-1H-imidazole-4-carbaldehyde [33016-47-6] in 30 ml of tetrahydrofuran is added. The mixture is stirred at −30° C. for 30 minutes, and then the reaction mixture is warmed to room temperature and quenched with saturated aqueous ammonium chloride solution. The phases are separated, and the aqueous phase is extracted with ethyl acetate (3×). The combined organic phases are washed with brine, dried with magnesium sulphate and evaporated. The title compound is obtained as a white solid from the residue by recrystallization from ethyl acetate. Rf=0.23 (CH$_2$Cl$_2$.2M NH$_3$ in EtOH 97:3); Rt=7.32.

The following compounds are prepared in analogy to the process described in Example 1:

3  4-(8-Methyl-5,6-dihydro-8H-imidazo[5,1-c][1,4]oxazin-8-yl)benzonitrile starting from 4-[1-hydroxy-1-(1-trityl-1H-imidazol-4-yl)ethyl]benzonitrile. Beige solid; Rf=0.26 (dichloromethane-2M ammonia in ethanol 97:3); Rt=4.54.

The starting material is prepared as follows:

a) 4-[1-Hydroxy-1-(1-trityl-1H-imidazol-4-yl)-ethyl]benzonitrile 12.98 mmol of methylmagnesium bromide solution (3M in diethyl ether) are added dropwise to a solution of 11.80 mmol of 4-(1-trityl-1H-imidazol-4-carbonyl)benzonitrile in 50 ml of tetrahydrofuran at −30° C. The cooling bath is removed and the mixture is stirred at room temperature for 1 hour. The reaction mixture is diluted with 100 ml of dichloromethane, and 100 ml of saturated aqueous ammonium chloride solution are added. The phases are separated and the aqueous phase is extracted with dichloromethane (1×). The combined organic phases are dried over magnesium sulphate and evaporated. The title compound is obtained without further purification as a white foam from the residue. Rf=0.15 (heptane-ethyl acetate 1:1), Rt=7.40.

b) 4-(1-Trityl-1H-imidazol-4-carbonyl)benzonitrile

A solution of 27.20 mmol of 4-[hydroxy-(1-trityl-1H-imidazol-4-yl)methyl]benzonitrile (Example 1d) in 100 ml of dichloromethane is mixed with 272.00 mmol of manganese (IV) oxide and heated to reflux for 2 hours. The reaction mixture is allowed to cool and is filtered through kieselguhr. The kieselguhr is washed with 100 ml of dichloromethane, and the combined organic phases are evaporated. The title compound is obtained without further purification as a white solid from the residue. Rf=0.13 (heptane-ethyl acetate 4:1), Rt=8.39.

5  4-(5,6-Dihydro-8H-imidazo[5,1-c][1,4]oxazin-8-yl)-2-fluorobenzonitrile starting from 2-fluoro-4-iodobenzonitrile [137553-42-5].

7  8-(4-Nitrophenyl)-5,6-dihydro-8H-imidazo[5,1-c][1,4]oxazine starting from 1-iodo-4-nitrobenzene [636-98-6]. Tetrahydrofuran is used instead of N,N-dimethylformamide as solvent in stage c

9  8-(4-Methanesulphonylphenyl)-5,6-dihydro-8H-imidazo[5,1-c][1,4]oxazine starting from 1-iodo-4-methanesulphonylbenzene [64984-08-3].

10  4-(5,6-Dihydro-8H-imidazo[5,1-c][1,4]oxazin-8-yl)-2,6-difluorobenzonitrile starting from 2,6-difluoro-4-iodobenzonitrile [14743-50-3].

11  4-(5,6-Dihydro-8H-imidazo[5,1-c][1,4]oxazin-8-yl)-2-methoxybenzonitrile starting from 4-iodo-2-methoxybenzonitrile [677777-44-5].

12  8-Benzo[b]thiophen-3-yl-5,6-dihydro-8H-imidazo[5,1-c][1,4]oxazine starting from 3-iodobenzo[b]thiophene [36748-88-6].

13  8-(7-Fluorobenzofuran-3-yl)-5,6-dihydro-8H-imidazo[5,1-c][1,4]oxazine starting from 3-bromo-7-fluorobenzofuran [1288851-92-3].

14  8-Pyridin-4-yl-5,6-dihydro-8H-imidazo[5,1-c][1,4]oxazine starting from 4-iodopyridine [15854-87-2].

15  4-(6,6-Dimethyl-5,6-dihydro-8H-imidazo[5,1-c][1,4]oxazin-8-yl)benzonitrile starting from ethyl 2-[(4-cyanophenyl)-(1-trityl-1H-imidazol-4-yl)methoxy]-2-methylpropionate.

The starting materials are prepared as follows:

a) Ethyl 2-[(4-cyanophenyl)(1-trityl-1H-imidazol-4-yl)methoxy]-2-methylpropionate 4.00 mmol of lithium diisopropylamine (2M in tetrahydrofuran) are added to a solution of 4.00 mmol of ethyl 2-[(4-cyanophenyl)(1-trityl-1H-imidazol-4-yl)methoxy]propionate in 40 ml of tetrahydrofuran and 5 ml of hexamethylphosphoric triamide (HMPA) at −78° C. The mixture is stirred at −78° C. for 15 minutes, and 4.00 mmol of methyl iodide are added. The reaction mixture is stirred at −78° C. for 30 minutes and warmed to room temperature over 2 hours. the reaction mixture is diluted with dichloromethane, and saturated aqueous ammonium chloride solution is added. The phases are separated and the aqueous phase is extracted with dichloromethane (1×). The combined organic phases are dried with sodium sulphate and evaporated. The title compound is identified from the residue on the basis of the Rf by flash chromatography (SiO$_2$ 60F).

b) Ethyl 2-[(4-cyanophenyl)(1-trityl-1H-imidazol-4-yl)methoxy]propionate

The title compound is prepared in analogy to Example 1c starting from ethyl 2-bromopropionate [535-11-5] and 4-[hydroxy-(1-trityl-1H-imidazol-4-yl)methyl]benzonitrile (Example 1d).

17  8-(3,4-Difluorophenyl)-5,6-dihydro-8H-imidazo[5,1-c][1,4]oxazine starting from 3,4-difluoro-1-iodobenzene [64248-58-4]. White wax.

19  3-(5,6-Dihydro-8H-imidazo[5,1-c][1,4]oxazin-8-yl)benzonitrile starting from 3-iodobenzonitrile [69113-59-3]. Brown oil. Rf=0.20 (dichloromethane-2M ammonia in ethanol 97:3); Rt=4.12.

20  4-(5,6-Dihydro-8H-imidazo[5,1-c][1,4]oxazin-8-yl)phthalonitrile starting from 4-iodophthalonitrile [69518-17-8].

21 4-(8-(4-Cyanophenyl)-5,6-dihydro-8H-imidazo[5,1-c][1,4]oxazin-8-yl)benzonitrile starting from 4-[hydroxy-(4-cyanophenyl)(1-trityl-1H-imidazol-4-yl)methyl]benzonitrile. Whitish solid. Rf=0.14 (dichloromethane-2M ammonia in ethanol 97:3); Rt=5.66.

The starting materials are prepared as follows:

a) 4-[Hydroxy-(4-cyanophenyl)(1-trityl-1H-imidazol-4-yl)methyl]benzonitrile 4-(1-Trityl-1H-imidazol-4-carbonyl)benzonitrile (Example 3b) is reacted with 4-iodobenzonitrile [3058-39-7] in analogy to Example 1d. The title compound is obtained as a white solid. Rt=7.9.

23 4-(5,6-Dihydro-8H-imidazo[5,1-c][1,4]oxazin-8-yl)naphthalene-1-carbonitrile starting from 4-iodonaphthalene-1-carbonitrile [140456-96-8]. Yellowish solid. Rf=0.13 (dichloromethane-2M ammonia in ethanol 95:5); Rt=5.49.

The following compound is prepared in analogy to the process described in Examples 1 and 3:

22 4-(8-Phenyl-5,6-dihydro-8H-imidazo[5,1-c][1,4]oxazin-8-yl)benzonitrile starting from 4-(1-trityl-1H-imidazol-4-carbonyl)benzonitrile (Example 3b) and phenyl-magnesium bromide [100-58-3]. Whitish solid. Rf=0.23 (dichloromethane-2M ammonia in ethanol 97:3); Rt=5.84.

Example 2

4-(5,6-Dihydro-8H-imidazo[5,1-c][1,4]thiazin-8-yl)benzonitrile

The title compound is obtained as a white solid in analogy to Example 1 from ethyl [(4-cyanophenyl)(1-trityl-1H-imidazol-4-yl)methylsulphanyl]acetate.

Rf=0.19 (dichloromethane-2M ammonia in ethanol 97:3); Rt=4.74.

The starting materials are prepared as follows:

a) Ethyl [(4-cyanophenyl)(1-trityl-1H-imidazol-4-yl)methylsulphanyl]acetate 1.80 mmol of triphenylmethyl chloride [76-83-5] and 1.92 mmol of diisopropylethylamine are added to a solution of 1.46 mmol of ethyl [(4-cyanophenyl)(1H-imidazol-4-yl)methyl-sulphanyl]acetate in 20 ml of N,N-dimethylformamide at room temperature. The reaction mixture is stirred at room temperature for 16 hours, then poured into ice-water and extracted with ethyl acetate. The combined organic phases are washed with brine, dried with sodium sulphate and evaporated. The title compound is obtained as a white solid from the residue by flash chromatography ($SiO_2$ 60F). Rf=0.36 (ethyl acetate-heptane 1:1); Rt=8.13.

b) Ethyl [(4-cyanophenyl)(1H-imidazol-4-yl)methyl-sulphanyl]acetate

A solution of 5.02 mmol of 4-[hydroxy-(1H-imidazol-4-yl)methyl]benzonitrile and 50.2 mmol of ethyl mercaptoacetate in 10 ml of trifluoroacetic acid is stirred at 70° C. for 24 hours. The reaction mixture is cooled to room temperature, poured into ice-water and neutralized with 4M sodium hydroxide solution. The mixture is extracted with ethyl acetate, and the combined organic phases are dried with sodium sulphate and evaporated. The title compound is obtained as an amber-coloured oil from the residue by flash chromatography ($SiO_2$ 60F). Rf=0.13 (dichloromethane-2M ammonia in ethanol 97:3); Rt=5.10.

c) 4-[Hydroxy-(1H-imidazol-4-yl)-methyl]benzonitrile 36.2 mmol of 4-[hydroxy-(1-trityl-1H-imidazol-4-yl)methyl]benzonitrile (Example 1d) are suspended in 100 ml of tetrahydrofuran. 7.2 ml of 6M hydrochloric acid are added to the suspension, and the reaction mixture is heated to reflux for 16 hours. The reaction mixture is cooled to room temperature and the solid is filtered off. The mother liquor is evaporated and the residue is taken up in water, basified with 4M sodium hydroxide solution and extracted with tert-butyl methyl ether. The aqueous phase is evaporated and thoroughly dried. The crude product is obtained as a beige foam which is employed without further purification for the next stage. Rt=3.3.

The following compounds are prepared in analogy to the process described in Example 2:

4 4-(8-Methyl-5,6-dihydro-8H-imidazo[5,1-c][1,4]thiazin-8-yl)benzonitrile starting from 1-(1-trityl-1H-imidazol-4-yl)ethanone [116795-55-2]. White solid.

Rf=0.29 (dichloromethane-2M ammonia in ethanol 97:3); Rt=4.96.

6 4-(5,6-Dihydro-8H-imidazo[5,1-c][1,4]thiazin-8-yl)-2-fluorobenzonitrile starting from 2-fluoro-4-iodobenzonitrile [137553-42-5].

Example 8

8-[4-(1H-Tetrazol-5-yl)phenyl]-5,6-dihydro-8H-imidazo[5,1-c][1,4]oxazine 3.34 mmol of trimethylsilyl azide are added to a solution of 0.17 mmol of 4-(5,6-dihydro-8H-imidazo[5,1-c][1,4]oxazin-8-yl)benzonitrile (Example 1) and 0.017 mmol of dibutyltin oxide in 4.0 ml of toluene. The reaction mixture is heated at 125° C. overnight. It is cooled to room temperature and evaporated. The title compound is identified from the residue on the basis of the Rf by flash chromatography ($SiO_2$ 60F).

Example 16

8-(4-Fluorophenyl)-5,6-dihydro-8H-imidazo[5,1-c][1,4]oxazine 4.33 mmol of 8-(4-fluorophenyl)-2-trityl-5,6-dihydro-8H-imidazo[5,1-c][1,4]oxazin-2-ium mesylate are taken up in 10 ml of glacial acetic acid, and the solution is heated at 100° C. for 16 hours. The reaction solution is cooled to room temperature and poured into ice-cold 4M sodium hydroxide solution. The mixture is extracted with dichloromethane. The combined organic phases are dried with sodium sulphate and evaporated. The title compound is obtained as a white solid from the residue by flash chromatography ($SiO_2$ 60F) and subsequent digestion with diethyl ether. Rf=0.29 (dichloromethane-2M ammonia in ethanol 95:5); Rt=4.42.

The starting materials are prepared as follows:

a) 8-(4-Fluorophenyl)-2-trityl-5,6-dihydro-8H-imidazo[5,1-c][1,4]oxazin-2-ium mesylate The title compound is obtained in analogy to Example 1 from 4-fluoro-1-iodobenzene [352-34-1].

Example 18

1-[4-(5,6-Dihydro-8H-imidazo[5,1-c][1,4]oxazin-8-yl)phenyl]ethanone 3 mmol of methylmagnesium bromide solution (3M in diethyl ether) are added to a solution of 0.97 mmol of 4-(5,6-dihydro-8H-imidazo[5,1-c][1,4]oxazin-8-yl)-N-methoxy-N-methyl-benzamide in 10 ml of absolute tetrahydrofuran under argon. The reaction solution is stirred at room temperature for 4 hours and then poured into saturated aqueous ammonium chloride solution and extracted with tert-butyl methyl ether. The combined organic phases are dried over magnesium sulphate and evaporated. The title compound is obtained as a beige solid from the residue by flash chromatography ($SiO_2$ 60F). Rf=0.19 (dichloromethane-2M ammonia in ethanol 97:3); Rt=4.10.

The starting materials are prepared as follows:

a) 4-(5,6-Dihydro-8H-imidazo[5,1-c][1,4]oxazin-8-yl)-N-methoxy-N-methylbenzamide 9.30 mmol of thionyl chloride are added to a solution of 3.10 mmol of 4-(5,6-dihydro-8H-imidazo[5,1-c][1,4]oxazin-8-yl)benzoic acid in 5 ml of chloroform. The reaction mixture is heated to reflux for 3 hours and then evaporated. The residue is stripped with toluene and then taken up in 10 ml of dichloromethane. The reaction solution is cooled to 0-5° C., and 3.10 mmol of N,O-dimethylhydroxylamine hydrochloride, followed by 15.5 mmol of diisopropylethylamine, are added. The reaction mixture is stirred at room temperature for 16 hours and filtered through Hyflo, and the filtrate is evaporated. The title compound is obtained as a yellowish oil from the residue by flash chromatography ($SiO_2$ 60F).

Rf=0.13 (dichloromethane-2M ammonia in ethanol 97:3); Rt=4.00.

b) 4-(5,6-Dihydro-8H-imidazo[5,1-c][1,4]oxazin-8-yl)benzoic acid

A solution of 3.10 mmol of 4-(5,6-dihydro-8H-imidazo[5,1-c][1,4]oxazin-8-yl)benzonitrile (Example 1) in 5 ml of ethanol is mixed with 3.1 ml of 2M sodium hydroxide solution. The reaction solution is heated to reflux for 24 hours. The reaction mixture is cooled to room temperature, neutralized with 2M hydrochloric acid and evaporated. The crude product is employed without further purification for the next stage. Rt=3.79.

Example 24

4-(5,6-Dihydro-8H-imidazo[5,1-c][1,4]oxazin-8-yl)benzonitrile

The racemic compound 4-(5,6-dihydro-8H-imidazo[5,1-c][1,4]oxazin-8-yl)benzonitrile (Example 1) is fractionated into the enantiomers by chiral preparative HPLC. The title compound is isolated as the enantiomer which elutes second. Rt*=8.22.

* HPLC Method:

Column: 250×50 mm CHIRALPAK® AD 20 μm

Mobile phase: $CO_2$/methanol 80:20

Flow rate: 240 ml/min

Detection: UV 230 nm

Temperature: 25° C.

Pressure: 150 bar

The invention claimed is:
1. A compound of the formula

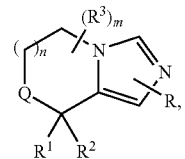

(I)

in which

R is deuterium, halogen, or hydrogen;

$R^1$ is aryl-$C_0$-$C_4$-alkyl, which radical is unsubstituted or substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, unsubstituted or substituted aryl, aryl-$C_0$-$C_4$ alkoxycarbonyl, cyano, halogen, unsubstituted or substituted heterocyclyl, hydroxy, nitro, oxide, oxo, tri-$C_1$-$C_4$ alkylsilyl, trifluoromethoxy or trifluoromethyl;

$R^2$ is a) deuterium, halogen, hydroxy, cyano or hydrogen; or is b) $C_2$-$C_8$ alkenyl, $C_2$-$C_8$ alkynyl, $C_1$-$C_8$ alkoxy, $C_1$-$C_4$ alkoxycarbonyl-$C_1$-$C_4$ alkyl, $C_1$-$C_8$ alkyl, $C_0$-$C_4$ alkylcarbonyl, aryl-$C_0$-$C_4$ alkyl, carboxy-$C_1$-$C_4$ alkyl, $C_3$-$C_8$ cycloalkyl, which radicals are unsubstituted or substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, unsubstituted or substituted aryl, aryl-$C_0$-$C_4$ alkoxycarbonyl, cyano, halogen, unsubstituted or substituted heterocyclyl, hydroxy, nitro, oxide, oxo, tri-$C_1$-$C_4$ alkylsilyl, trifluoromethoxy or trifluoromethyl;

$R^3$ is $C_1$-$C_8$ alkyl;

Q is oxygen;

m is a number 0, 1 or 2;

n is a number 1;

or a pharmaceutically acceptable salt thereof where $R^1$ is not $C_1$-$C_8$ alkyl-substituted aryl if $R^2$ is hydrogen.

2. A compound according to claim 1, which corresponds to the formula

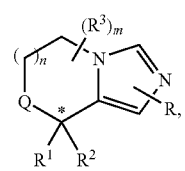

(Ia)

or a pharmaceutically acceptable salt thereof, where the meanings of the substituents R, $R^1$, $R^2$, $R^3$, Q, m and n are as indicated for compounds of the formula (I) according to claim 1, and * designates an asymmetric carbon atom and which compound shows an aldosterone synthase and/or 11-β-hydroxylase inhibitory activity at least 10 times higher, than the compound of the formula (Ia) with the opposite configuration around the asymmetric carbon atom labelled "*".

3. A compound according to claim 2, and which compound shows an aldosterone synthase and/or 11-β-hydroxylase inhibitory activity at least 20 times higher than the compound of the formula (Ia) with the opposite configuration around the asymmetric carbon atom labelled "*".

4. A compound according to claim 3, and which compound shows an aldosterone synthase and/or 11-β-hydroxylase inhibitory activity at least 40 times higher than the compound of the formula (Ia) with the opposite configuration around the asymmetric carbon atom labelled "*".

5. A compound according to claim 1, where R is deuterium or hydrogen.

6. A compound according to claim 2, where R is deuterium or hydrogen.

7. A compound according to claim 1, where $R^1$ is unsubstituted or substituted phenyl, unsubstituted or substituted naphthyl, benzofuranyl, benzo[b]thiophenyl, benzoimidazolyl, benzo[d]isothiazolyl, benzo[d]isoxazolyl, benzo[b]thiophenyl, imidazolyl, indazolyl, oxazolyl, pyridyl, pyrrolyl, thiazolyl or thiophenyl.

8. A compound according to claim 2, where $R^1$ is unsubstituted or substituted phenyl, unsubstituted or substituted naphthyl, benzofuranyl, benzo[b]thiophenyl, benzoimidazolyl, benzo[d]isothiazolyl, benzo[d]isoxazolyl, benzo[b]thiophenyl, imidazolyl, indazolyl, oxazolyl, pyridyl, pyrrolyl, thiazolyl or thiophenyl.

9. A compound according to claim 1, where $R^2$ is $C_1$-$C_8$ alkoxy, hydroxy, $C_1$-$C_8$ alkyl, unsubstituted or substituted aryl-$C_0$-$C_4$ alkyl, deuterium, halogen, cyano or hydrogen.

10. A compound according to claim 2, where $R^2$ is $C_1$-$C_8$ alkoxy, hydroxy, $C_1$-$C_8$ alkyl, unsubstituted or substituted aryl-$C_0$-$C_4$ alkyl, deuterium, halogen, cyano or hydrogen.

11. A method for treatment of a patient having hypokalaemia, hypertension, congestive heart failure, acute or chronic renal failure, cardiovascular restenosis, atherosclerosis, metabolic syndrome, adiposity (obesity), vasculitis, primary or secondary hyperaldosteronism, nephropathy, myocardial infarction, coronary heart disease, increased collagen formation, fibrosis, vascular or coronary tissue changes, secondary to high blood pressure, endothelial dysfunction, or oedemas secondary to cirrhosis, nephrosis or congestive heart failure, which comprises administering a therapeutically effective amount of a compound of the formula (I) or a pharmaceutically acceptable salt thereof according to claim 1 to the patient.

12. A method for treatment of a patient having hypokalaemia, hypertension, congestive heart failure, acute or chronic renal failure, cardiovascular restenosis, atherosclerosis, metabolic syndrome, adiposity (obesity), vasculitis, primary or secondary hyperaldosteronism, nephropathy, myocardial infarction, coronary heart disease, increased collagen formation, fibrosis, vascular or coronary tissue changes, secondary to high blood pressure, endothelial dysfunction, or oedemas secondary to cirrhosis, nephrosis or congestive heart failure, which comprises administering a therapeutically effective amount of a compound of the formula (Ia) or a pharmaceutically acceptable salt thereof according to claim 2 to the patient.

13. A method for treatment of a patient having Cushing's syndrome or excessive or persistent cortisol secretion, which comprises administering a therapeutically effective amount of a compound of the formula (I) or a pharmaceutically acceptable salt thereof according to claim 1 to the patient.

14. A method for treatment of a patient having Cushing's syndrome or excessive or persistent cortisol secretion, which comprises administering a therapeutically effective amount of a compound of the formula (Ia) or a pharmaceutically acceptable salt thereof according to claim 2 to the patient.

15. A pharmaceutical composition comprising a compound of the formula (I) or a pharmaceutically acceptable salt thereof according to claim 1, and a conventional excipient.

16. A pharmaceutical composition comprising a compound of the formula (Ia) or a pharmaceutically acceptable salt thereof according to claim 2, and a conventional excipient.

17. A pharmaceutical composition in the form of a product or of a kit comprising individual components consisting a) of a compound of the formula (I) or a pharmaceutically acceptable salt thereof according to claim 1, and b) at least one pharmaceutical form whose active ingredient has a blood pressure-lowering, an inotropic, a metabolic or a lipid-lowering effect.

18. A pharmaceutical composition in the form of a product or of a kit comprising individual components consisting a) of a compound of the formula (Ia) or a pharmaceutically acceptable salt thereof according to claim 2, and b) at least one pharmaceutical form whose active ingredient has a blood pressure-lowering, an inotropic, a metabolic or a lipid-lowering effect.

* * * * *